(12) United States Patent  (10) Patent No.: US 8,498,700 B2
Coggins  (45) Date of Patent: Jul. 30, 2013

(54) DISPOSABLE INTERNAL DEFIBRILLATION ELECTRODES

(75) Inventor: Scott R. Coggins, Littleton, MA (US)

(73) Assignee: Convidien LP, Mansfield, MA (US)

( * ) Notice: Subject to any disclaimer, the term of this patent is extended or adjusted under 35 U.S.C. 154(b) by 386 days.

(21) Appl. No.: 12/883,655

(22) Filed: Sep. 16, 2010

(65) Prior Publication Data

US 2012/0071938 A1 Mar. 22, 2012

(51) Int. Cl.
*A61N 1/39* (2006.01)

(52) U.S. Cl.
USPC ............... 607/5; 607/142; 607/148; 607/152

(58) Field of Classification Search
USPC ...................................... 607/5, 142, 152, 148
See application file for complete search history.

(56) References Cited

U.S. PATENT DOCUMENTS

| 5,213,113 | A | * | 5/1993 | Hlinsky ..................... 607/152 |
| 7,120,503 | B2 | | 10/2006 | Miller et al. |
| 7,742,828 | B2 | * | 6/2010 | Gadsby et al. ............... 607/142 |
| 2003/0191501 | A1 | * | 10/2003 | Miller et al. ..................... 607/5 |
| 2007/0255381 | A1 | | 11/2007 | Meyer |
| 2007/0255382 | A1 | | 11/2007 | Meyer et al. |

* cited by examiner

*Primary Examiner* — Carl H Layno
*Assistant Examiner* — Jon Eric C Morales
(74) *Attorney, Agent, or Firm* — Lisa E. Winsor, Esq.

(57) ABSTRACT

A disposable electrode paddle assembly is provided and includes a shaft having a proximal end and a distal end; a handle assembly supported at the proximal end of the shaft; a spoon supported at the distal end of the shaft; an electrical conductor extending from the handle assembly and establishing an electrical connection at the spoon; and an electrode assembly selectively, electrically connectable to the electrical connection provided at the spoon; wherein the electrode assembly includes a layer of silver/silver-chloride (Ag/AgCl) having one of an increasing and decreasing density extending in a radially outward direction.

30 Claims, 5 Drawing Sheets

DISPOSABLE INTERNAL DEFIBRILLATION ELECTRODES

BACKGROUND

1. Field of Invention

The present disclosure relates to electrodes and, inure particularly, to disposable internal defibrillation electrode/lead paddle assemblies configured for external transthorasic defibrillation, pacing, and electrocardiogram acquisition.

2. Background

Electrodes, which are typically used in medical applications, generally include a conductor and a connector. The connector is attached at one end to the conductor and includes a plug at the other end to be plugged into a defibrillator or other device. The conductor is often covered or coated in a conductive gel, which enhances its ability to adhere to a patient's skin.

During open-heart surgery, a pair of internal defibrillation paddles is used to restart the patient's heart. In use, each paddle is held in direct contact against the myocardium (heart muscle). An electric discharge is passed from one electrode through the patient's heart to a second electrode in an effort to restart the patient's heart.

However, prior to use, electrodes must be sterilized to eliminate patient infection. Modern sterilization methods use heat or chemical agents, such as ethylene oxide. The methods and materials used degrade the electrodes, thus limiting their useful life. Most manufacturers specify a maximum service life for electrodes. However, there is no convenient mechanism for users to measure and track the number of sterilization cycles an electrode experiences. Therefore, there is no easy way to determine if the service life of the electrodes has been exceeded.

Therefore, a need exists for electrodes that may used on a patient once and then disposed of.

SUMMARY

According to an aspect of the present disclosure, a disposable electrode paddle assembly is provided and includes a shaft having a proximal end and a distal end; a handle assembly supported at the proximal end of the shaft; a spoon supported at the distal end of the shaft; an electrical conductor extending from the handle assembly and establishing an electrical connection at the spoon; and an electrode assembly selectively, electrically connectable to the electrical connection provided at the spoon. The electrode assembly includes a layer of silver/silver-chloride (Ag/AgCl) having one of an increasing and decreasing density extending in a radially outward direction.

The layer of silver/silver-chloride (Ag/AgCl) may include a first area having a first density and a second area having a second density, greater than the first density, and may be disposed radially inward or radially outward of the first area.

The second area may be substantially centrally located within an outer diameter of the electrode assembly. The first area may be substantially circular. The second area may be spaced a radial distance inward from an outer edge of the electrode.

The silver/silver-chloride (Ag/AgCl) layer may be composed of about 62% silver (Ag) and about 38% chloride (Cl). The silver/silver-chloride (Ag/AgCl) layer may have a thickness of less than 10 μm.

The first area may have a higher impedance than the second area. The second area may have a higher impedance than the first area.

An outer edge of the first area may include an annular array of spikes extending at least partially therearound; and an outer edge of the second area may include an annular array of spikes extending at least partially therearound.

The electrode assembly may further include at least one lead wire in electrical communication with the layer of silver/silver-chloride (Ag/AgCl). The at least one lead wire may be in operative communication with the electrical connection at the spoon.

According to another aspect of the present disclosure, a disposable electrode paddle assembly is provided and includes a shaft having a proximal end and a distal end; a handle assembly supported at the proximal end of the shaft; a spoon supported at the distal end of the shaft; an electrical conductor extending from the handle assembly and establishing an electrical connection at the spoon; and an electrode assembly selectively, electrically connectable to the electrical connection provided at the spoon. The electrode assembly includes a first substrate constructed from an electrically insulative material; a second substrate constructed, at least partially, from a conductive material; a third substrate being a carbon/vinyl film; a fourth substrate being a conductive hydrogel; and a single layer of silver/silver-chloride (Ag/AgCl) interposed between adjacent substrates. The layer of silver/silver-chloride (Ag/AgCl) has one of an increasing and decreasing density extending in a radially outward direction.

The first substrate may be constructed from an X-ray transparent material.

The layer of silver/silver-chloride (Ag/AgCl) may be disposed between the second substrate and the third substrate. The layer of silver/silver-chloride (Ag/AgCl) may be disposed between the third substrate and the fourth substrate.

The third substrate may be constructed from a flexible sheet of graphite filled polyvinyl chloride film having a thickness from about 2 mils to about 4 mils.

The silver/silver-chloride (Ag/AgCl) layer may be composed of 62% silver (Ag) and 38% chloride (Cl). The silver/silver-chloride (Ag/AgCl) layer may have a thickness of less than 10 μm.

The layer of silver/silver-chloride (Ag/AgCl) may include a first area having a first density and a second area having a second density, greater than the first density, and may be disposed one of radially inward and radially outward of the first area.

The second area may be substantially centrally located within an outer diameter of the electrode assembly. The first area may be substantially circular. The second area may be spaced a radial distance inward from an outer edge of the electrode.

The first area may have a higher impedance than the second area. The second area may have a higher impedance than the first area.

An outer edge of the first area may include an annular array of spikes extending at least partially therearound; and an outer edge of the second area may include an annular array of spikes extending at least partially therearound.

The electrode assembly may further include at least one lead wire in electrical communication with the layer of silver/silver-chloride (Ag/AgCl).

The at least one lead wire may be in operative communication with the electrical connection at the spoon.

BRIEF DESCRIPTION OF THE DRAWINGS

Various embodiments of the disposable internal defibrillation electrode paddle assembly are described herein with reference to the drawings wherein.

DETAILED DESCRIPTION

Figure 1:
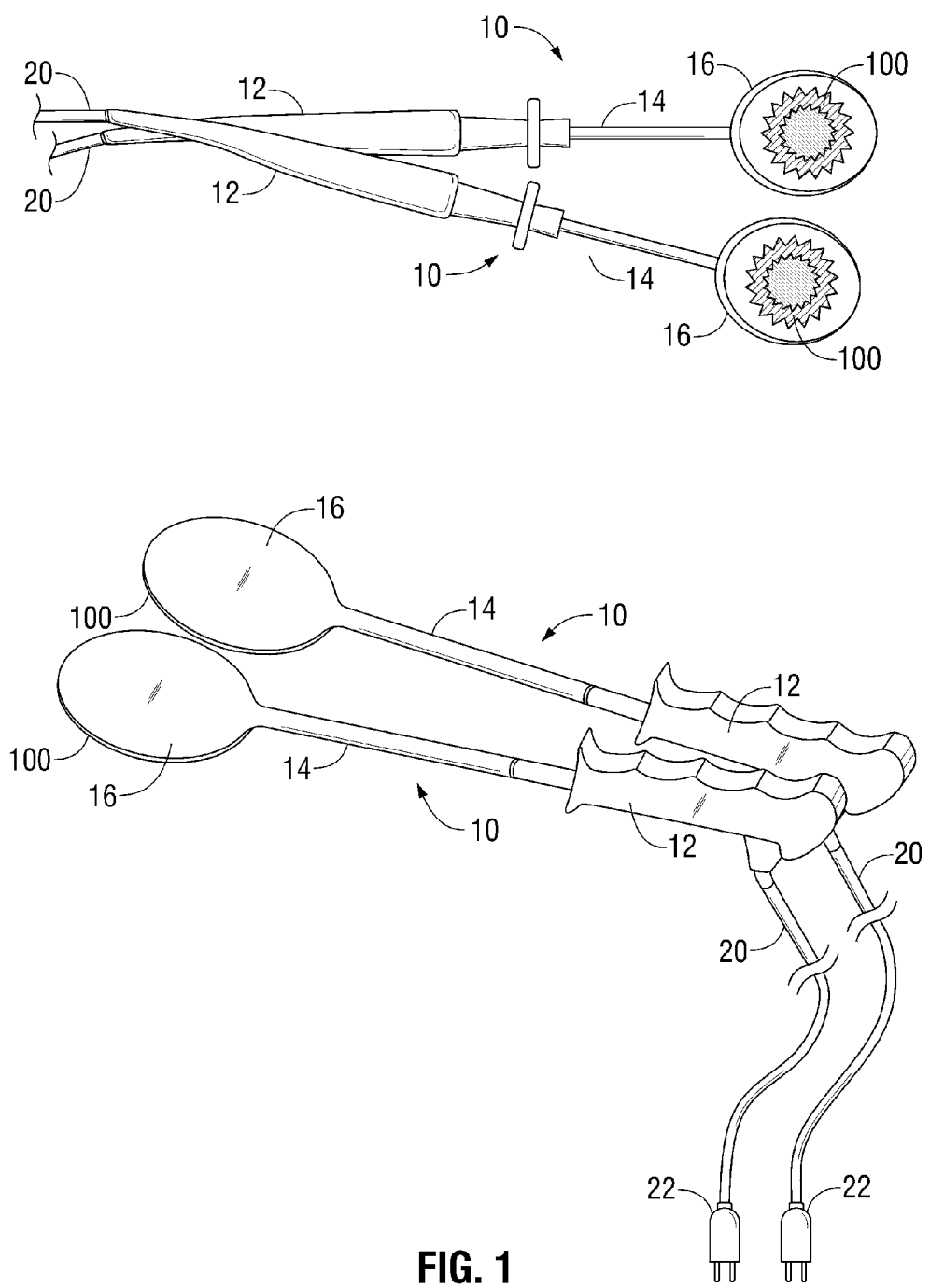
FIG. 1 is a perspective view of an internal defibrillation electrode paddle assembly, according to an embodiment of the present disclosure.

Embodiments of the presently disclosed disposable internal defibrillation electrode paddle assembly will now be described in detail with reference to the drawing figures wherein like reference numerals identify similar or identical elements.

As illustrated in FIG. 1, a pair of defibrillator electrode paddle assemblies, according to an embodiment of the present disclosure, is illustrated with each electrode paddle assembly being generally designated as 10. Each defibrillation electrode paddle assembly 10 includes a handle 12, a shaft 14 extending from the handle 12, and a spoon 16 supported on an end of the shaft 14. Each defibrillation electrode paddle assembly 10 includes a cable 20 extending from handle 12 and including a plug 22 for connection with a defibrillator monitor (not shown). Each cable 20 extends through shaft 14 to spoon 16 and provides an electrical contact region for spoon 16. Each spoon 16 is configured to selectively support/connect an electrode assembly 100 thereto and electrically contact the end of cable 20.

Electrode 100, and alternate embodiments thereof, will be further described with reference to FIGS. 2-5. It is noted that the electrodes described in FIGS. 2, 3, and 6 are constructed to have a higher impedance near the edges thereof as compared to a center thereof.

Figure 2:
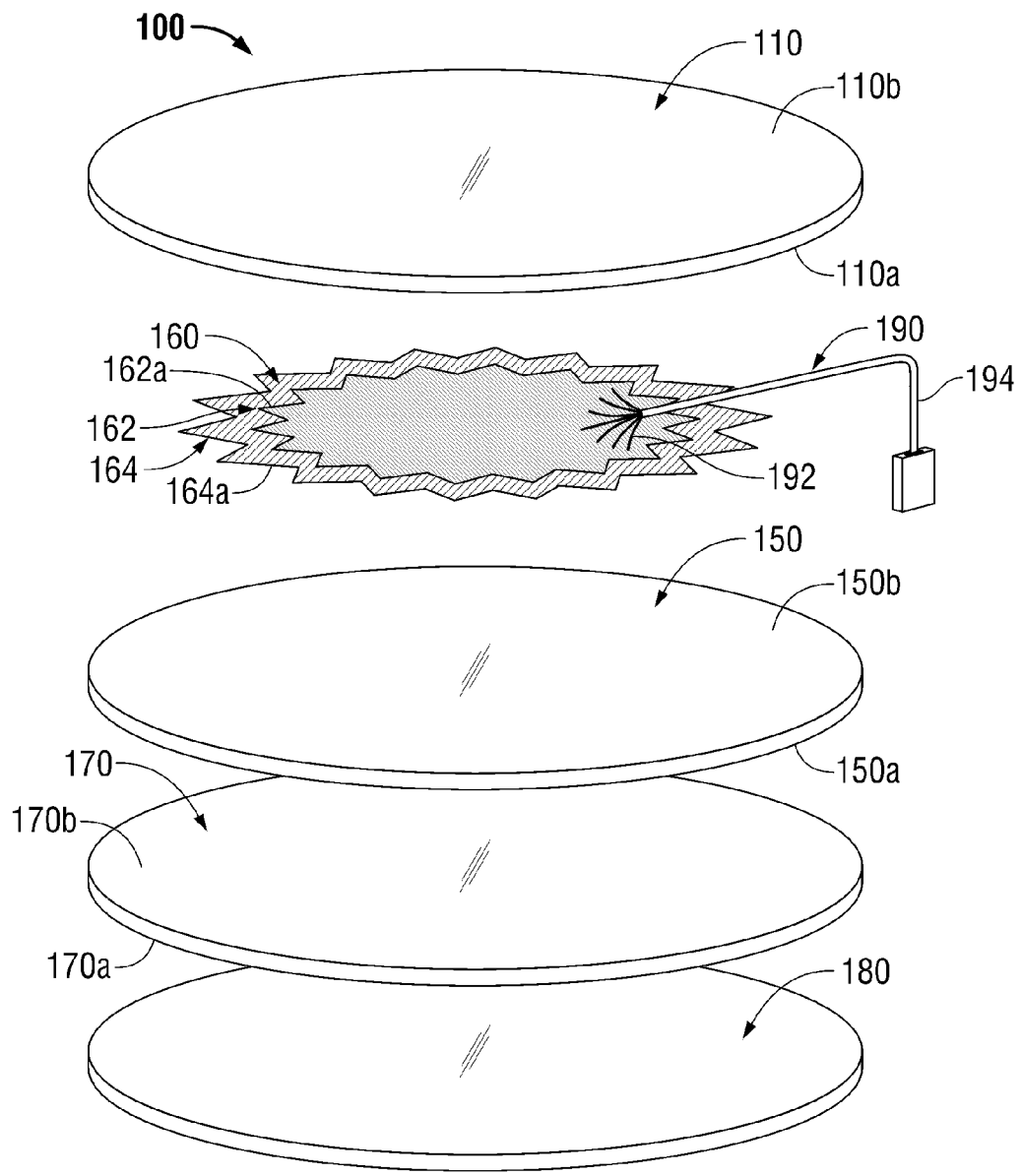
FIG. 2 is a perspective view, with layers separated, of an electrode, according to an embodiment of the present disclosure, for use with the internal defibrillation electrode paddle assembly.
Figure 3:
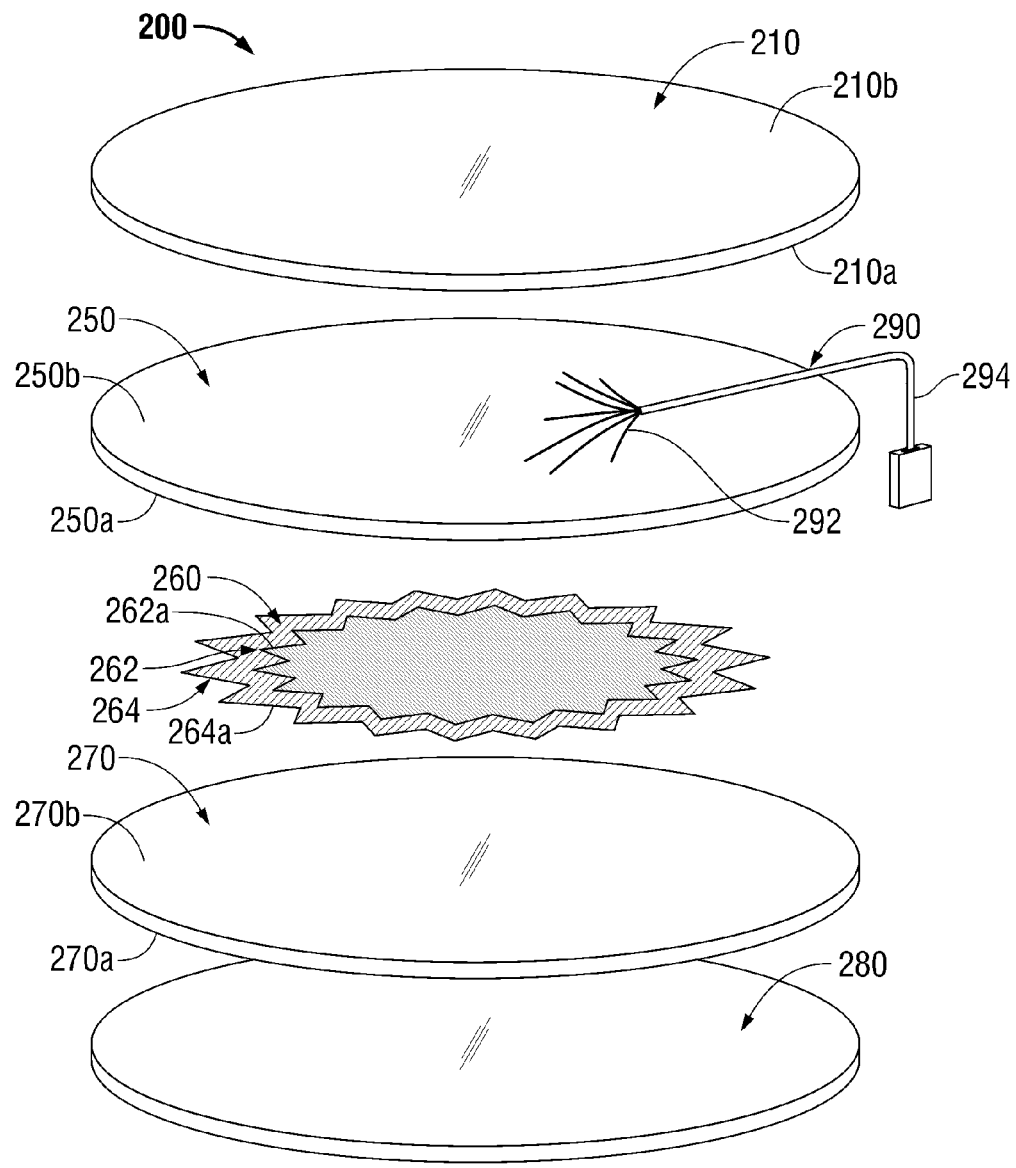
FIG. 3 is a perspective view, with layers separated, of an electrode, according to another embodiment of the present disclosure, for use with the internal defibrillation electrode paddle assembly.

Referring to FIG. 2, a first embodiment of the electrode assembly is generally designated as 100. Electrode assembly 100 includes a backing substrate or cover 110 defining a first or front side 110a facing a subject (not shown) and a second or back side 110b, opposite first side 110a and facing away from the subject.

Cover 110 is fabricated from an electrically insulative and X-ray transparent material having sufficient strength and rigidity to support an electrode. Cover 110 may be clear in order to enable a user to see through the cover 110. Cover 110 is circular or disc-shaped although other shapes such as square, rectangular, and triangular are contemplated. Cover 110 may have any regular or irregular shape according to a desired use. One skilled in the art may contemplate fabricating cover 110 from a plurality of suitable materials in accordance with desired applications. In one embodiment, the backing may be a low cost material so that disposal after single patient use is not cost prohibitive. In one embodiment, cover 110 is a nonconductive foam, such as polyethylene foam having a thickness of about 1/16 of an inch.

Electrode assembly 100 includes a conductive layer 150 defining a first or front side 150a facing a subject (not shown) and a second or back side 150b, opposite first side 150a and facing away from the subject. Conductive layer 150 may be any conductive material such as carbon/vinyl film, conductive rubber, a metallic foil such as aluminum foil, tin foil, silver foil, and copper foil and may be dimensioned to have a first diameter that is smaller than a diameter of cover 110. Carbon/vinyl film 150 is in contact with Ag/AgCl coating 160 and with first side 110a of cover 110 located radially outward of perimetrical region 164 of Ag/AgCl coating 160.

Carbon/vinyl film 150 is formed of a thin flexible sheet of graphite filled polyvinyl chloride film having a thickness of the order of about two to four mils. Carbon/vinyl film 150 is a commercial product available and purchased from Exopack™, LLC, 345 Cedar Springs Ave., Spartanburg, S.C. Carbon/vinyl film 150, including coating 160 of Ag/AgCl ink, is inherently radiolucent. One skilled in the art may contemplate fabricating carbon/vinyl film 150 from a plurality of suitable materials in accordance with desired applications.

Electrode assembly 100 includes a coating of silver/silver-chloride (Ag/AgCl) ink 160 disposed on second or back side 150b of carbon/vinyl film 150. Ag/AgCl coating 160 is printed on second or back side 150b of carbon/vinyl film 150. Ag/AgCl coating 160 includes a central region 162 of continuous 100% or substantially continuous coverage and a perimetrical region 164 having less than substantially continuous coverage. In one embodiment, the silver/silver-chloride ink coverage in the perimetrical region 164 may be about 50%. Silver/silver-chloride ink may be deposited in the perimetrical region 164 by conventional methods in a desired pattern which may be regular, irregular, random and combinations thereof. In one embodiment, the ink in the perimetrical region 164 may be a speckle or spray pattern. In another embodiment, the ink in the perimetrical region may be a regular pattern such as squares, triangles, stripes of similar or varying thickness. The density of the ink applied to the perimetrical region may vary throughout the region and may form a gradient. For example, the density of the ink may be higher in the portion of the perimetrical region 164 adjacent the central region 162 and lower at one or more locations further from the central region 162. Alternatively, the density of the ink may be lower in the portion of the perimetrical region 164 adjacent the central region 162 and higher at one or more locations further from the central region 162. The embodiment of FIG. 2 illustrates a solid silver portion 162 surrounded by the perimetrical region 164 having a substantially uniform silver/silver chloride coverage of about 50% silver, both deposited on the unprinted conductive layer.

Central region 162 of Ag/AgCl coating 160 is shown as substantially circular including an array of spikes 162a therearound extending radially outward, although it is understood that other shapes and cross sectional areas are contemplated depending on a desired use. The spikes may be sized and shaped for a particular purpose and may, but need not be identical. The spikes may, but need not be spaced equidistantly about the outer periphery of the central region 162. Although the spikes are shown to originate from a V-Shape and culminate in a point, the spikes may have a variety of shapes, for example originating from a U shape and/or culminating in a rounded or blunt tip. Central region 162 of Ag/AgCl coating 160 defines a second diameter that is smaller than the first diameter of carbon/vinyl film 150.

Perimetrical region 164 of Ag/AgCl coating 160 is shown as substantially circular including an array of spikes 164a therearound extending radially outward, although it is understood that other shapes and cross sectional areas are contemplated depending on a desired use. The spikes may, but need not be spaced equidistantly about the outer periphery. Although the spikes are shown to originate from a V-Shape and culminate in a point, the spikes may have a variety of shapes, for example originating from a U-Shape and/or culminating in a rounded or blunt tip. The overall shape of the perimetrical region may, but need, not have the same general shape as the central region. For example, the location of the spikes in the perimetrical region may, but need not, align with the spikes extending from the central region. Perimetrical region 164 of Ag/AgCl coating 160 defines a third diameter that is smaller than the first diameter of carbon/vinyl film 150 and larger than the second diameter of central region 162. Perimetrical region 164 is sized to define an area between the outer edge thereof and the outer edge of carbon/vinyl film 150 that is free from any coating of Ag/AgCl ink.

Ag/AgCl ink is applied in a coating to second or back side 150b of carbon/vinyl film 150 by conventional methods such as silk screening, flexographic printing, spray coating, transfer coating, rotogravure, and off set letter press. The thickness of the Ag/AgCl coating 160 may be any desired thickness suitable for a particular purpose and sufficient to provide good electrical conductivity without substantially impairing the X-ray transparency of the electrode member. Additionally, Ag/AgCl coating 160 has a thickness which does not noticeably effect or change the flexibility of electrode assembly 100. In one embodiment, the Ag/AgCl coating has a thickness of about ten microns.

Ag/AgCl coating 160 may be composed of about 62% Ag and about 38% AgCl. In one embodiment, the Ag/AgCl coating may be composed of about 50% Ag and about 50% Cl. In yet another embodiment, the Ag/AgCl coating may be comprised of about 83% AG and about 17% Cl. Such a composition of Ag/AgCl may result in a coating of Ag/AgCl having no or insufficient structural integrity on its own and thus is conventionally applied to a backing layer in order to form any pattern. As such, Ag/AgCl coating 160 is not typically an independent layer. One skilled in the art may contemplate using any types of conductive materials in any number of different compositions to achieve desired results. For example, the conductive silver coating may be formed as a free standing film and could replace the carbon/vinyl film.

Electrode assembly 100 is electrically connectable with a first end 192 of a lead wire 190 interposed between cover 110 and Ag/AgCl coating 160. A second end 194 of lead wire 190 extends from a side of electrode assembly 100 and is configured to electrical connection to cable 20, via a plug, a contact pad/tab or the like.

Electrode assembly 100 includes a conductive hydrogel 170 defining a first or front side 170a facing a subject (not shown) and a second or back side 170b, opposite first side 170a and facing away from the subject, wherein back side 170b of hydrogel 170 is in contact with first side 150a of conductive/vinyl film 150. Hydrogel 170 provides an electromechanical interface between electrode assembly 100 and the subject (not shown). Hydrogel 170 may also adhesively connect electrode assembly 100 to the subject.

Additionally, electrode assembly 100 may include a release liner 180 underlying hydrogel 170 to protect hydrogel 170 prior to use.

Referring to FIG. 3, a second embodiment of an electrode assembly is generally designated as 200. Electrode assembly 200 includes a backing substrate or cover 210 defining a first or front side 210a facing a subject (not shown) and a second or back side 210b, opposite first side 210a and facing away from the subject.

Cover 210 is fabricated from an electrically insulative substrate and may be an X-ray transparent material and may have sufficient strength and rigidity to support an electrode. Cover 210 may be clear in order to enable a user to see through the cover 210. Cover 210 may have any regular or irregular shape suitable for a particular use. Cover 210 is circular or disc-shaped first diameter although other shapes such as square, rectangular, and triangular are contemplated. One skilled in the art may contemplate fabricating cover 210 from a plurality of suitable materials in accordance with desired applications. In one embodiment, the backing may be a low cost material so that disposal after single patient use is not cost prohibitive. In one embodiment, cover 110 is a nonconductive foam, such as polyethylene foam having a thickness of about 1/16 of an inch.

Electrode assembly 200 includes a conductive layer 250 defining a first or front side 250a facing a subject (not shown) and a second or back side 250b, opposite first side 250a and facing away from the subject. The conductive layer may be formed of any conductive material such as carbon/vinyl conductive rubber, a metallic foil such as aluminum foil, silver foil, tin foil and copper foil and may be dimensioned to have a diameter that is smaller than a diameter of cover 210. In one embodiment a carbon/vinyl film 250 is in contact with front side 210a of cover 210.

Carbon/vinyl film 250 is formed of a thin flexible sheet of graphite filled polyvinyl chloride film having a thickness of the order of about two to four mils. Carbon/vinyl film 250 is a commercial product available and purchased from Exopack™, LLC, 345 Cedar Springs Ave., Spartanburg, S.C. One skilled in the art may contemplate fabricating carbon/vinyl film 250 from a plurality of suitable materials in accordance with desired applications.

Electrode assembly 200 is electrically connectable with a first end 292 of a lead wire 290 interposed between cover 210 and carbon/vinyl film 250. A second end 294 of lead wire 290 extends from a side of electrode assembly 200 and is configured to electrical connection to cable 20, via a plug, a contact pad/tab or the like.

Electrode assembly 200 includes a coating of silver/silver-chloride (Ag/AgCl) ink 260 disposed on first or front side 250a of carbon/vinyl film 250. Ag/AgCl coating 260 is screen printed on front side 250a of carbon/vinyl film 250. Ag/AgCl coating 260 includes a central region 262 of continuous 100% coverage, or substantially continuous, and a perimetrical region 264 having less than substantially continuous coverage. In one embodiment, the silver/silver-chloride ink coverage in the perimetrical region 264 may be about 50%. Silver/silver-chloride ink may be deposited in the perimetrical region 264 by conventional methods in a desired pattern which may be regular, irregular, random and combinations thereof. In one embodiment, the ink in the perimetrical region 264 may be a speckle or spray pattern. In another embodiment, the ink in the perimetrical region may be a regular pattern such as squares, triangles, stripes of similar or varying thickness. The density of the ink applied to the perimetrical region may vary throughout the region and may form a gradient. For example, the density of the ink may be higher in the portion of the perimetrical region 264 adjacent the central region 262 and lower at one or more locations further from the central region 262. Alternatively, the density of the ink may be lower in the portion of the perimetrical region 264 adjacent the central region 262 and higher at one or more locations further from the central region 262.

Central region 262 of Ag/AgCl coating 260 is substantially circular and includes an array of spikes 262a therearound extending radially outward. Central region 262 of Ag/AgCl coating 260 defines a second diameter that is smaller than a first diameter of carbon/vinyl film 250.

Perimetrical region 264 of Ag/AgCl coating 260 is shown as substantially circular including an array of spikes 264a therearound extending radially outward, although it is understood that other shapes and cross sectional areas are contemplated depending on a desired use. The spikes may, but need not be spaced equidistantly about the outer periphery. Although the spikes are shown to originate from a V-shape and culminate in a point, the spikes may have a variety of shapes, for example of originating from a U-shape and/or culminating in a rounded or blunt tip. The overall shape of the perimetrical region may but need not have the same general shape as the central region. For example, the location of the spikes in the perimetrical region may, but need not, align with the spikes extending from the central region. Perimetrical region 264 of Ag/AgCl coating 260 defines a third diameter that is smaller than the first diameter of carbon/vinyl film 250 and larger than the second diameter of central region 262. Perimetrical region 264 is sized to define an area between the outer edge thereof and the outer edge of carbon/vinyl film 250 that is free from any coating of Ag/AgCl ink.

Ag/AgCl ink is applied in a coating to first or front side 250a of carbon/vinyl film 250 by silk screening, flexographic printing, spray coating, and transfer coating. The thickness of the Ag/AgCl coating 260 may be any desired thickness suitable for a particular purpose and sufficient to provide good electrical conductivity without substantially impairing the X-ray transparency of the electrode member. Additionally, Ag/AgCl coating 260 has a thickness which does not noticeably effect or change the flexibility of electrode assembly 200. In one embodiment, the Ag/AgCl coating has a thickness of about ten microns.

Ag/AgCl coating 260 is composed of about 62% Ag and about 38% AgCl. In one embodiment the Ag/AgCl coating may be composed of about 50% Ag and about 50% Cl. In yet another embodiment, the Ag/AgCl coating may be composed of about 83% Ag and about 17% Cl. Such a composition of Ag/AgCl results in a coating of Ag/AgCl having no or insufficient structural integrity on its own and thus is conventionally applied to a backing layer in order to form any pattern. As such, Ag/AgCl coating 260 is not typically an independent layer. Carbon/vinyl film 250, including coating 260 of Ag/AgCl ink, is inherently radiolucent. One skilled in the art may contemplate using any types of conductive materials in any number of different compositions to achieve desired results. For example, the conductive silver coating may be formed as a free standing film and could replace the carbon/vinyl film.

Electrode assembly 200 includes a conductive hydrogel 270 defining a first or front side 270a facing a subject (not shown) and a second or back side 270b, opposite first side 270a and facing away from the subject, wherein back side 270b of hydrogel 270 is in 100% direct contact with front side 250a of conductive/vinyl film 250 located radially outward of perimetrical region 264 of Ag/AgCl coating 260, in approximately 50% direct contact with skin side 250a of conductive/vinyl film 250 located in perimetrical region 264, and in 100% direct contact with central region 262 of Ag/AgCl coating 260. Hydrogel 270 provides an electromechanical interface between electrode assembly 200 and the subject (not shown). Hydrogel 270 may also adhesively connect electrode assembly 200 to the subject.

Electrode assembly 200 may include a release liner 280 underlying hydrogel 270 to protect hydrogel 270 prior to use.

Figure 4:
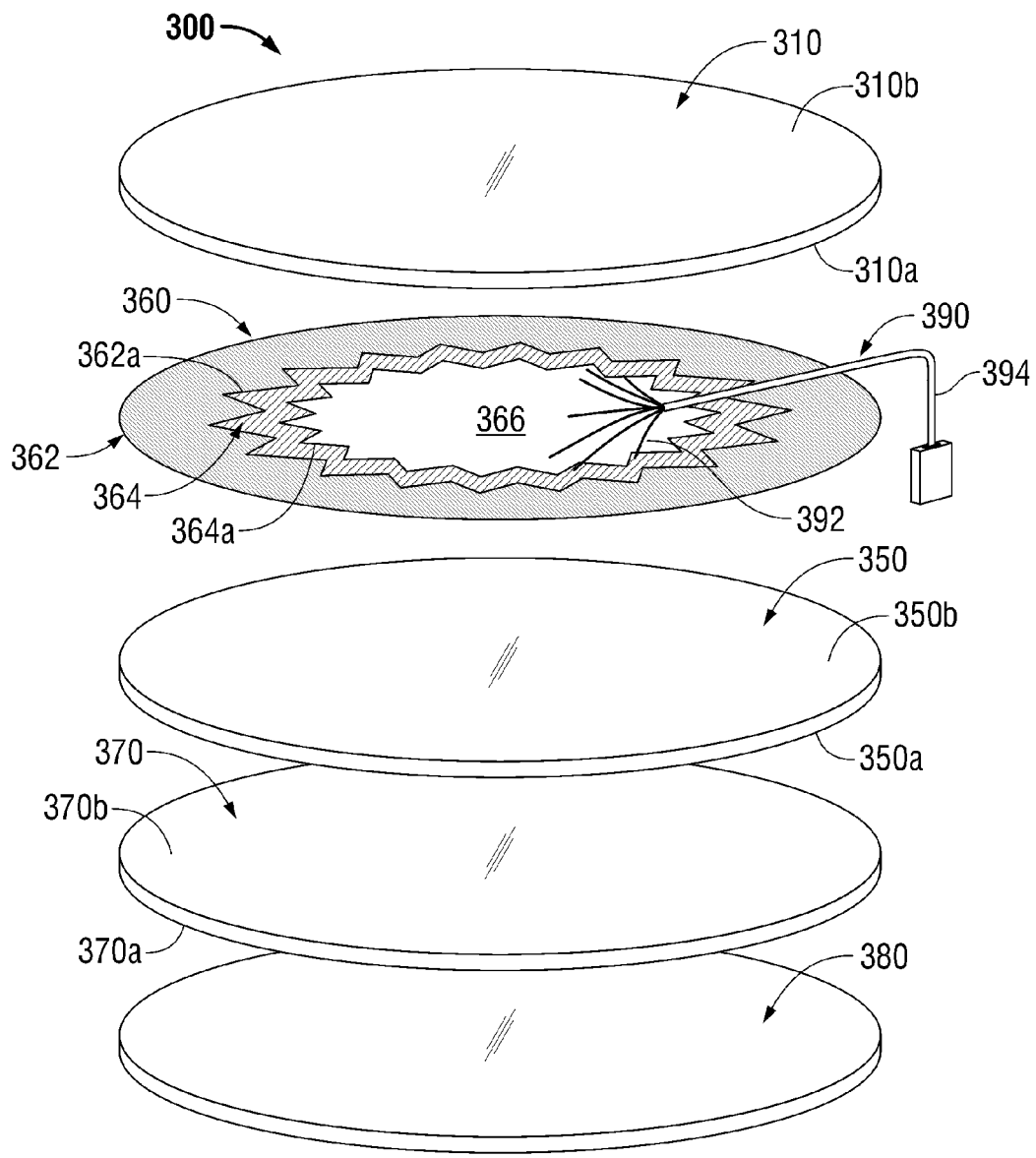
FIG. 4 is a perspective view, with layers separated, of an electrode, according to yet another embodiment of the present disclosure, for use with the internal defibrillation electrode paddle assembly.
Figure 5:
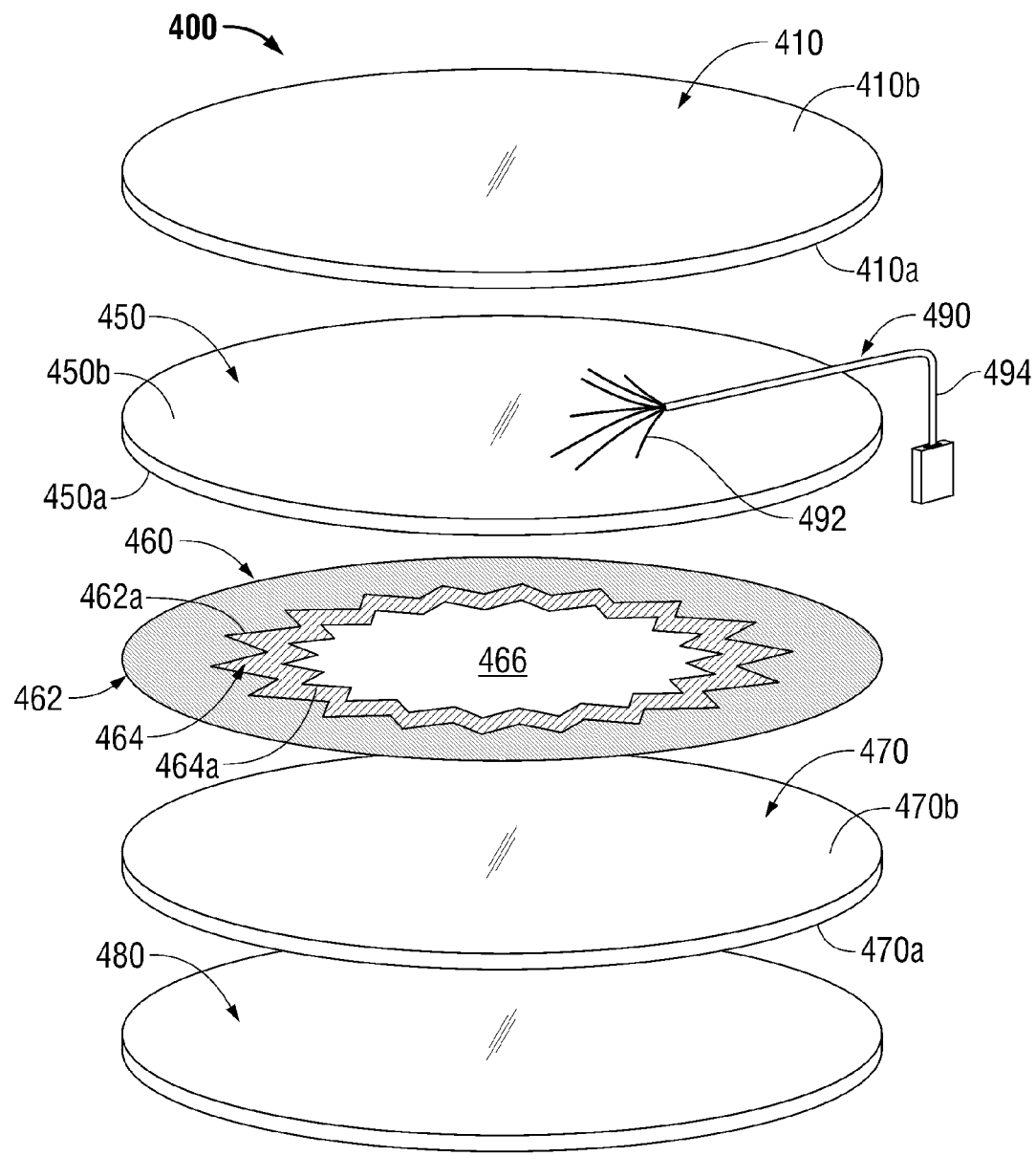
FIG. 5 is a perspective view, with layers separated, of an electrode, according to still another embodiment of the present disclosure, for use with the internal defibrillation electrode paddle assembly.

Alternatively to electrode assemblies 100 and 200, electrode assemblies may be constructed to have a higher impedance near a center thereof as compared to the edges thereof, as illustrated in FIGS. 4 and 5.

With reference to FIG. 4, a third embodiment of an electrode assembly is generally designated as 300. Electrode assembly 300 includes a backing substrate or cover 310 defining a first or front side 310a facing a subject (not shown) and a second or back side 310b, opposite first side 310a and facing away from the subject.

Cover 310 is fabricated from an electrically insulative substrate and may be an X-ray transparent material and have sufficient strength and rigidity to support an electrode. Cover 310 may be clear in order to enable a user to see through the cover 310. Cover 310 may have any regular or irregular shape suitable for a particular purpose. Cover 310 is circular or disc-shaped, although other shapes such as square, rectangular, and triangular are contemplated. One skilled in the art may contemplate fabricating cover 310 from a plurality of suitable materials in accordance with desired applications. In one embodiment, the backing may be a low cost material so that disposal after a single use is not cost prohibitive. In one embodiment, cover 310 is a nonconductive foam such as polyethylene foam having a thickness of about $\frac{1}{16}$ of an inch.

Electrode assembly 300 includes a conductive layer 350 defining a first or front side 350a facing a subject (not shown) and a second or back side 350b, opposite first side 350a and facing away from the subject. Conductive layer 350 may be formed of any conductive material, such as carbon/vinyl film, conductive rubber, a metallic foil such as aluminum foil, silver foil, tin foil and copper foil and may be dimensioned to have a first diameter that is smaller than a diameter of cover 310. Carbon/vinyl film 350 is in contact with an Ag/AgCl coating 360 and with front side 310a of cover 310 located within an open central region 366 of Ag/AgCl coating 360.

Carbon/vinyl film 350 is formed of a thin flexible sheet of graphite filled polyvinyl chloride film having a thickness of the order of about two to four mils. Carbon/vinyl film 350 is a commercial product available and purchased from Exopack™, LLC, 345 Cedar Springs Ave., Spartanburg, S.C. Carbon/vinyl film 350, including coating 360 of Ag/AgCl ink, is inherently radiolucent. One skilled in the art may contemplate fabricating carbon/vinyl film 350 from a plurality of suitable materials in accordance with desired applications.

Electrode assembly 300 includes a coating of silver/silver-chloride (Ag/AgCl) ink 360 disposed on second or back side 350b of carbon/vinyl film 350. Ag/AgCl coating 360 is deposited on second or back side 350b of carbon/vinyl film 350. Ag/AgCl coating 360 includes an outer ring or region 362 of continuous 100% coverage or substantially continuous and an inner ring or region 364 having less than substantially continuous coverage. Ag/AgCl coating 360 defines an open central region 366 that is free of Ag/AgCl ink. In one embodiment, the silver/silver-chloride ink coverage in the inner ring 364 may be about 50%. Silver/silver-chloride ink may be deposited in the inner ring 364 by conventional methods in a desired pattern which may be regular, irregular, random and combinations thereof. In one embodiment, the ink in the inner ring 364 may be a speckle or spray pattern. In another embodiment, the ink in the inner ring may be a regular pattern such as squares, triangles, stripes of similar or varying thickness. The density of the ink applied to the inner ring may vary throughout the region and may form a gradient. For example, the density of the ink in the inner ring may be higher in the region adjacent the central region 366 and lower at one or more locations adjacent the outer ring 362. Alternatively, the density of the ink may be lower in the region adjacent the central region 366 and higher at one or more locations adjacent the outer ring 362. Outer ring 362 of Ag/AgCl coating 360 is shown as substantially circular including an array of spikes 362a therearound extending radially inward, although it is understood that other shapes and cross sectional areas are contemplated depending on the desired use. Outer ring 362 of Ag/AgCl coating 360 extends radially inward to a second diameter that is smaller than the first diameter of carbon/vinyl film 350. The spikes may be sized and shaped for a particular purpose and may, but need not be identical to one another. The spikes may, but need not be spaced equidistantly about the inner periphery of the outer ring. Although the spikes are shown to originate from a V-shape and culminate in at point, the spikes may have a variety of shapes, for example, originating from a U shape and/or culminating in a rounded or blunt tip.

Inner ring or region 364 of Ag/AgCl coating 360 is shown as substantially circular including an array of spikes 364a therearound extending radially inward, although it is understood that other shapes and cross sectional areas are contemplated depending on the desired use. Inner ring or region 364 of Ag/AgCl coating 360 extends radially inward to a third diameter that is smaller than the second inner diameter of outer ring 362 and defines the open central region 366 that is free from any coating of Ag/AgCl ink. The spikes may be sized and shaped for a particular purpose and may, but need not be identical to one another. The spikes may, but need not be spaced equidistantly about the inner periphery of the inner ring. Although the spikes are shown to originate from a V-shape and culminate in at point, the spikes may have a variety of shapes, for example, originating from a U-shape and/or culminating in a rounded or blunt tip.

Ag/AgCl ink is applied in a coating to second or back side 350b of carbon/vinyl film 350 by conventional methods such as silk screening, flexographic printing, spray coating, transfer coating, rotogravure and off set letter press. The thickness of the Ag/AgCl coating 360 may be any desired thickness suitable for a particular purpose and sufficient to provide good electrical conductivity without substantially impairing the X-ray transparency of the electrode member. Additionally, Ag/AgCl coating 360 has a thickness which does not noticeably effect or change the flexibility of electrode assembly 300. In one embodiment, the AG/AgCl coating has a thickness of about ten microns.

Ag/AgCl coating 360 is composed of about 62% Ag and about 38% AgCl. In one embodiment, the Ag/AgCl coating may be composed of about 50% Ag and about 50% AgCl. In yet another embodiment, the Ag/AgCl coating may be composed of about 83% Ag and about 17% Cl. Such a composition of Ag/AgCl results in a coating of Ag/AgCl having no or insufficient structural integrity on its own and is conventionally applied to a backing layer in order to form any pattern. As such, Ag/AgCl coating 360 is not typically an independent layer. One skilled in the art may contemplate using any types of conductive materials in any number of different compositions to achieve desired results. For example, the conductive silver coating may be formed is a free standing film and could replace the carbon/vinyl film.

Electrode assembly 300 is electrically connectable with a first end 392 of a lead wire 390 interposed between cover 310 and Ag/AgCl coating 360. A second end 394 of lead wire 390 extends from a side of electrode assembly 300 and is configured to electrical connection to cable 20, via a plug, a contact pad/tab or the like.

Electrode assembly 300 includes a conductive hydrogel 370 defining a first or front side 370a facing a subject (not shown) and a second or back side 370b, opposite first side 370a and facing away from the subject, wherein back side 370b of hydrogel 370 is in contact with front side 350a of conductive/vinyl film 350. Hydrogel 370 provides an electromechanical interface between electrode assembly 300 and the subject (not shown). Hydrogel 370 also adhesively connects electrode assembly 300 to the subject.

Electrode assembly 300 may include a release liner 380 underlying hydrogel 370 to protect hydrogel 370 prior to use.

Referring to FIG. 5, a fourth embodiment of an electrode assembly is generally designated as 400. Electrode assembly 400 includes a backing substrate or cover 410 defining a first or front side 410a facing a subject (not shown) and a second or back side 410b, opposite first side 410a and facing away from the subject.

Cover 410 is fabricated from an electrically insulative and may be an X-ray transparent material and have sufficient strength and rigidity to support an electrode. Cover 410 may be clear in order to enable a user to see through the cover 410. Cover 410 is circular or disc-shaped defining a first diameter, although other shapes such as square, rectangular, and triangular are contemplated. Cover 410 may have any regular or irregular shape suitable for a desired purpose. One skilled in the art may contemplate fabricating cover 410 from a plurality of suitable materials in accordance with desired applications. In one embodiment, the backing may be a low cost material so that disposal after single patient use is not cost prohibitive. In one embodiment, cover 410 is non conductive foam, such as polyethylene form having a thickness of about ¹⁄₁₆ of an inch.

Electrode assembly 400 includes a conductive layer film 450 defining a first or front side 450a facing a subject (not shown) and a second or back side 450b, opposite first side 450a and facing away from the subject. Conductive layer may be formed of any conductive material such as carbon/vinyl film, conductive rubber, a metallic foil such as aluminum foil, silver foil, tin foil and copper foil and may be dimensioned to have a diameter that is smaller than a diameter of cover 410. In one embodiment, the carbon/vinyl film 450 is in contact with front side 410a of cover 410.

Carbon/vinyl film 450 is formed of a thin flexible sheet of graphite filled polyvinyl chloride film having a thickness of the order of about two to four mils. Carbon/vinyl film 450 is a commercial product available and purchased from Exopack™, LLC, 345 Cedar Springs Ave., Spartanburg, S.C. One skilled in the art may contemplate fabricating carbon/vinyl film 450 from a plurality of suitable materials in accordance with desired applications.

Electrode assembly 400 is electrically connectable with a first end 492 of a lead wire 490 interposed between cover 410 and carbon/vinyl film 450. A second end 494 of lead wire 490 extends from a side of electrode assembly 400 and is configured to electrical connection to cable 20, via a plug, a contact pad/tab or the like.

Electrode assembly 400 includes a coating of silver/silver-chloride (Ag/AgCl) ink 460 disposed on first or skin side 450a of carbon/vinyl film 450. Ag/AgCl coating 460 is screen printed on skin side 450a of carbon/vinyl film 450. Ag/AgCl coating 460 includes an outer ring or region 462 of continuous 100% coverage or substantially continuous and an inner ring or region 464 of having less than substantially continuous coverage. Ag/AgCl coating 460 defines an open central region 466 that is free of Ag/AgCl ink. In one embodiment, the silver/silver-chloride ink coverage in the inner ring 464 may be about 50%. Silver/silver-chloride ink may be deposited in the inner ring 464 by conventional methods in a desired pattern which may be regular, irregular, random and combinations thereof. In one embodiment, the ink in the inner ring 464 may be a speckle or spray pattern. In another embodiment, the ink in the inner ring may be a regular pattern such as squares, triangles, stripes of similar or varying thickness. The density of the ink applied to the inner ring may vary throughout the region and may form a gradient. For example, the density of the ink in the inner ring may be higher in the region adjacent the central region 466 and lower at one or more locations adjacent the outer ring 462. Alternatively, the density of the ink may be lower in the region adjacent the central region 466 and higher at one or more locations adjacent the outer ring 462.

Outer ring 462 of Ag/AgCl coating 460 is shown as substantially circular including an array of spikes 462a therearound extending radially inward, although it is understood that other shapes and cross sectional areas are contemplated depending on a particular use. Outer ring 462 of Ag/AgCl coating 460 extends radially inward to a second diameter that is smaller than the first diameter of cover 410. The spikes may be sized and shaped for a particular purpose and may, but need not be identical to one another. The spikes may, but need not be spaced equidistantly about the inner periphery of the outer ring. Although the spikes are shown to originate from a V-shape and culminate in at point, the spikes may have a variety of shapes, for example, originating from a U-shape and/or culminating in a rounded or blunt tip.

Inner ring or region 464 of Ag/AgCl coating 460 is shown as substantially circular and includes an array of spikes 464a therearound extending radially inward although other shapes and cross sectional areas are contemplated. Inner ring or region 464 of Ag/AgCl coating 460 extends radially inward to a third diameter that is smaller than the second inner diameter of outer ring 462 and defines the open central region 466 that is free from any coating of Ag/AgCl ink. The spikes may be sized and shaped for a particular purpose and may, but need not be identical to one another. The spikes may, but need not be spaced equidistantly about the inner periphery of the inner ring. Although the spikes are shown to originate from a V-shape and culminate in at point, the spikes may have a variety of shapes, for example, originating from a U-shape and/or culminating in a rounded or blunt tip.

Ag/AgCl ink is applied in a coating to skin side 450a of carbon/vinyl film 450 by conventional methods such as silk screening, flexographic printing spray coating, and transfer coating. The thickness of the Ag/AgCl coating 460 may be any desired thickness suitable for a particular purpose and sufficient to provide good electrical conductivity without substantially impairing the X-ray transparency of the electrode member. Additionally, Ag/AgCl coating 460 has a thickness which does not noticeably effect or change the flexibility of electrode assembly 400. In one embodiment, the Ag/AgCl coating as a thickness of about ten microns.

Ag/AgCl coating 460 is composed of about 62% Ag and about 38% AgCl. Such a composition of Ag/AgCl results in a coating of Ag/AgCl having no or insufficient structural integrity on its own and thus is conventionally applied to a backing layer in order to form any pattern. As such, Ag/AgCl coating 460 is not typically an independent layer. Carbon/vinyl film 450, including coating 460 of Ag/AgCl ink, is inherently radiolucent. One skilled in the art may contemplate using any types of conductive materials in any number of different compositions to achieve desired results.

Electrode assembly 400 includes a conductive hydrogel 470 defining a first or front side 470a facing a subject (not shown) and a second or back side 470b, opposite first side 470a and facing away from the subject, wherein back side 470b of hydrogel 470 is in 100% direct contact with front side 450a of conductive/vinyl film 450 disposed within open central region 466 of Ag/AgCl coating 460, in approximately 50% direct contact with skin side 450a of conductive/vinyl film 450 disposed in inner ring or region 464 of Ag/AgCl coating 460, and in 100% direct contact with outer ring or region 462 of Ag/AgCl coating 460. Hydrogel 470 provides an electromechanical interface between electrode assembly 400 and the subject (not shown). Hydrogel 470 may also adhesively connect electrode assembly 400 to the subject.

Electrode assembly 400 may include a release liner 480 underlying hydrogel 470 to protect hydrogel 470 prior to use.

As discussed above, electrode assemblies 100, 200, 300 and 400 are selectively, electrically connectable to spoon 16 of defibrillation electrode paddle assembly 10. In particular, electrode assemblies 100, 200, 300 and 400 are selectively, electrically connectable to cable 20 extending through handle 12 and shaft 14 of defibrillation electrode paddle assembly 10 for electrical connection to a defibrillator monitor (not shown). As so configured, following a surgical procedure or use, electrode assemblies 100, 200, 300 or 400 are detached from spoon 16 of defibrillation electrode paddle assembly 10 and discarded while defibrillation electrode paddle assembly 10 may be sterilized and/or re-sterilized.

Additionally, it is contemplated that different combinations of electrode assemblies 100, 200, 300 and 400 may be used as electrode assembly pairs for use with the pair of defibrillation electrode paddle assemblies 10 depending on the type of effect on the heart desired during the defibrillation.

In particular, electrode assemblies 100 and 200 may be used to improve conductivity to the center thereof and reduce conductivity to the edges thereof; electrode assemblies 300 and 400 may be used to improve conductivity to the edges thereof and reduce conductivity to the center thereof; or a combination of one electrode assembly 100, 200 and one electrode assembly 300, 400 in order to establish a degree of directionality to the conductivity.

It is to be understood that the foregoing description is merely a disclosure of particular embodiments and is in no way intended to limit the scope of the disclosure. Other possible modifications will be apparent to those skilled in the art and are intended to be within the scope of the present disclosure. For example the cover may be formed of a treated or untreated cloth so that the structural strength is creating as the layers are formed or combined. Similarly the Ag/AgCl coating described above may include gradual, continuous density gradient or a step gradient in which each step is uniformly coated. Other configurations of the Ag/AgCl coating contemplated include a cruciform pattern as well as other patterns disclosed in U.S. Pat. No. 7,742,828 issued on Jun. 22, 2010 and entitled Medical Electrode Suitable for High-Energy Stimulation, which is incorporated herein by reference in its entirety for all purposes. Moreover, the handle configuration of the present invention may include switches and/or controls for easy access by the user.

What is claimed is:

1. A disposable electrode paddle assembly, comprising:
a shaft having a proximal end and a distal end;
a handle assembly supported at the proximal end of the shaft;
a spoon supported at the distal end of the shaft;
an electrical conductor extending from the handle assembly and establishing an electrical connection at the spoon; and
an electrode assembly selectively, electrically connectable to the electrical connection provided at the spoon;
wherein the electrode assembly includes a layer of silver/silver-chloride (Ag/AgCl) having a first area and a second area, and having one of an increasing and decreasing density extending in a radially outward direction;
wherein an outer edge of the first area includes an annular array of spikes extending at least partially therearound; and
wherein an outer edge of the second area includes an annular array of spikes extending at least partially therearound.

2. The disposable electrode paddle assembly according to claim 1, wherein the first area has a first density and the second area has a second density, greater than the first density, and being disposed one of radially inward and radially outward of the first area.

3. The disposable electrode paddle assembly according to claim 2, wherein the second area is substantially centrally located within an outer diameter of the electrode assembly.

4. The disposable electrode paddle assembly according to claim 2, wherein the first area is substantially circular.

5. The disposable electrode paddle assembly according to claim 2, wherein the second area is spaced a radial distance inward from an outer edge of the electrode.

6. The disposable electrode paddle assembly according to claim 2, wherein the first area has a higher impedance than the second area.

7. The disposable electrode paddle assembly according to claim 2, wherein the second area has a higher impedance than the first area.

8. The disposable electrode paddle assembly according to claim 1, wherein the silver/silver-chloride (Ag/AgCl) layer is composed of about 62% silver (Ag) and about 38% chloride (Cl).

9. The disposable electrode paddle assembly according to claim 1, wherein the silver/silver-chloride (Ag/AgCl) layer is composed of about 50% silver (Ag) and about 50% chloride (Cl).

10. The disposable electrode paddle assembly according to claim 1, wherein the silver/silver-chloride (Ag/AgCl) layer is composed of about 83% silver (Ag) and about 17% chloride (Cl).

11. The disposable electrode paddle assembly according to claim 1, wherein the silver/silver-chloride (Ag/AgCl) layer has a thickness of less than 10 µm.

12. The disposable electrode paddle assembly according to claim 1, wherein the electrode assembly further comprises at least one lead wire in electrical communication with the layer of silver/silver-chloride (Ag/AgCl).

13. The disposable electrode paddle assembly according to claim 12, wherein the at least one lead wire is in operative communication with the electrical connection at the spoon.

14. A disposable electrode paddle assembly, comprising:
a shaft having a proximal end and a distal end;
a handle assembly supported at the proximal end of the shaft;
a spoon supported at the distal end of the shaft;
an electrical conductor extending from the handle assembly and establishing an electrical connection at the spoon; and
an electrode assembly selectively, electrically connectable to the electrical connection provided at the spoon, the electrode assembly including:
a first substrate constructed from an electrically insulative material;
a second substrate constructed, at least partially, from a conductive material;
a third substrate being a carbon/vinyl film;
a fourth substrate being a conductive hydrogel; and
a single layer of silver/silver-chloride (Ag/AgCl) interposed between adjacent substrates, the layer of silver/silver-chloride (Ag/AgCl) having a first area and a second area, and having one of an increasing and decreasing density extending in a radially outward direction;
wherein an outer edge of the first area includes an annular array of spikes extending at least partially therearound; and
wherein an outer edge of the second area includes an annular array of spikes extending at least partially therearound.

15. The disposable electrode paddle assembly according to claim 14, wherein the first substrate is constructed from an X-ray transparent material.

16. The disposable electrode paddle assembly according to claim 14, wherein the layer of silver/silver-chloride (Ag/AgCl) is disposed between the second substrate and the third substrate.

17. The disposable electrode paddle assembly according to claim 14, wherein the layer of silver/silver-chloride (Ag/AgCl) is disposed between the third substrate and the fourth substrate.

18. The disposable electrode paddle assembly according to claim 14, wherein the third substrate is constructed from a flexible sheet of graphite filled polyvinyl chloride film having a thickness from about 2 mils to about 4 mils.

19. The disposable electrode paddle assembly according to claim 14, wherein the silver/silver-chloride (Ag/AgCl) layer is composed of about 62% silver (Ag) and about 38% chloride (Cl).

20. The disposable electrode paddle assembly according to claim 14, wherein the silver/silver-chloride (Ag/AgCl) layer is composed of about 50% silver (Ag) and about 50% chloride (Cl).

21. The disposable electrode paddle assembly according to claim 14, wherein the silver/silver-chloride (Ag/AgCl) layer is composed of about 83% silver (Ag) and about 17% chloride (Cl).

22. The disposable electrode paddle assembly according to claim 14, wherein the silver/silver-chloride (Ag/AgCl) layer has a thickness of less than 10 µm.

23. The disposable electrode paddle assembly according to claim 14, wherein the first area has a first density and the second area has a second density, greater than the first density, and being disposed one of radially inward and radially outward of the first area.

24. The disposable electrode paddle assembly according to claim 23, wherein the first area is substantially circular.

25. The disposable electrode paddle assembly according to claim 23, wherein the second area is spaced a radial distance inward from an outer edge of the electrode.

26. The disposable electrode paddle assembly according to claim 23, wherein the first area has a higher impedance than the second area.

27. The disposable electrode paddle assembly according to claim 23, wherein the second area has a higher impedance than the first area.

28. The disposable electrode paddle assembly according to claim 23, wherein the electrode assembly further comprises at least one lead wire in electrical communication with the layer of silver/silver-chloride (Ag/AgCl).

29. The disposable electrode paddle assembly according to claim 28, wherein the at least one lead wire is in operative communication with the electrical connection at the spoon.

30. The disposable electrode paddle assembly according to claim 14, wherein the second area is substantially centrally located within an outer diameter of the electrode assembly.

\* \* \* \* \*